(12) United States Patent
Mayeresse (10) Patent No.: US 8,173,411 B2
(45) Date of Patent: *May 8, 2012

(54) DRYING PROCESS FOR PRESERVING AN ACTIVE AGENT AS A HIGHLY VISCOUS LIQUID

(75) Inventor: Yves Mayeresse, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 391 days.

This patent is subject to a terminal disclaimer.

(21) Appl. No.: 11/587,023

(22) PCT Filed: Apr. 28, 2005

(86) PCT No.: PCT/EP2005/004638

§ 371 (c)(1),
(2), (4) Date: Oct. 20, 2006

(87) PCT Pub. No.: WO2005/105978

PCT Pub. Date: Nov. 10, 2005

(65) Prior Publication Data

US 2007/0298052 A1    Dec. 27, 2007

(30) Foreign Application Priority Data

Apr. 30, 2004 (GB) .................................. 0409795.2

(51) Int. Cl.
*C12N 1/00* (2006.01)
*A61K 39/13* (2006.01)
*A61K 39/29* (2006.01)

(52) U.S. Cl. .................... 435/243; 424/217.1; 424/227.1

(58) Field of Classification Search .................. None
See application file for complete search history.

(56) References Cited

U.S. PATENT DOCUMENTS 7,927,858 B2 *  4/2011  Mayeresse ................... 435/243

FOREIGN PATENT DOCUMENTS

| WO | WO 96/40077 | 12/1996 |
|---|---|---|
| WO | WO 2004/039417 | 5/2004 |

OTHER PUBLICATIONS

Worrall, et al. Xero6ac: an ultra rapid method for the dehydration and preservation of live attenuated Rinderpest and Peste des Petits. Vaccine 19 (2001) 834-839.*
Kadam, et al. Effect of excipients on product characteristics and structure of lyophilized lasota vaccine. Indian Journal of Biotechnology 2005; 4 (1):106-114. Abstract Only.*

* cited by examiner

*Primary Examiner* — Stacy B. Chen
(74) *Attorney, Agent, or Firm* — Michael M. Conger (57) ABSTRACT

The present invention relates to a method of drying biological and other labile samples so that they can be preserved as a highly viscous liquid. The method involves the steps of preparing a preservation sample by dissolving/suspending an active agent in a solution of a stabilizing agent, subjecting the preservation sample to such temperature and pressure conditions that the preservation sample looses solvent by evaporation without freezing or bubbling to form a foam and removing solvent until the preservation sample dries to form a highly viscous liquid. The stabilizing solution comprises a glass forming polyol and a second component which decreases the flow rate of the highly viscous liquid formed by the method.

17 Claims, 2 Drawing Sheets

DRYING PROCESS FOR PRESERVING AN ACTIVE AGENT AS A HIGHLY VISCOUS LIQUID

The present invention relates to the preservation of biological and other labile samples as a highly viscous liquid. The highly viscous liquid is formed by preparing a preservation sample by dissolving/suspending an active agent in a solution of a stabilising agent, evaporating solvent from the preservation sample without freezing or foam formation and drying to form a highly viscous liquid. The stabilising agent comprises a glass forming polyol and a second component which decreases the flow rate of the highly viscous liquid formed during the process. Aspects of the invention include a method for preserving an active agent, highly viscous liquids comprising an active agent, vaccines comprising a highly viscous liquid and methods of making the vaccine.

There is a need to extend the stability and thus the shelf life of labile samples, particularly biological samples. Traditionally, this has been accomplished using the process of freeze drying in which a solution of the substance is made and the sample is frozen. During the primary drying phase, most of the water is removed by sublimation from ice under reduced pressure conditions and a porous 'cake' is formed. This is usually followed by a secondary drying phase when the pressure and temperature are changed and water is evaporated from the solid 'cake'. The resulting lyophilised sample has improved stability compared to a liquid formulation. However, the freeze drying process is lengthy, expensive and can be the rate limiting step in a production process.

Freeze drying can also lead to the loss of activity or antigenicity of some active agents. For certain biological materials such as live virus, there can be significant loss of activity during the freeze drying process (Pikal (1994) ACS Symposium 567: 120-133). Many freeze dried substances are still unstable at ambient temperature (Carpenter et al (1994) ACS Symposium 567; 134-147).

Damage caused by the process of freezing may be circumvented to some degree by the use of stabilising agents such as polyols. Further improvements on the process of lyophilisation have also been made by avoiding freezing the sample during the process and removing water by boiling (WO96/40077; U.S. Pat. No. 6,306,345). This method involves preparing a mixture of a glass-matrix forming material in a suitable solvent together with the sample to be preserved, evaporating bulk solvent from the mixture to obtain a syrup, exposing the syrup to a pressure and temperature sufficient to cause boiling of the syrup and removing residual solvent. Methods similar to this may be referred to as foam drying techniques. Such techniques will expose the sample to be preserved to stresses due to the formation and bursting of bubbles during the 'boiling' stage. Especially where labile substances are to be preserved, this may result in a loss of activity.

A similar method was described in U.S. Pat. No. 5,766,520, in which the process involves partially removing the water to form a viscous fluid and further subjecting the syrup to vacuum to cause it to 'boil' and further drying at temperatures substantially lower than 100° C. This method still suffers from some of the problems of conventional freeze-drying. When the process is carried out in a large freeze-dryer, samples will dry at different rates depending on their position on the shelf and this leads to different samples loosing different amount of activity during the drying process. This leads to a lack of consistency within a batch.

Trehalose is a polyol that is favoured for its stabilising properties. Trehalose is a naturally occurring, inert, non-reducing and non-toxic, glass-forming disaccharide that was initially found to be associated with the prevention of desiccation damage in some plants and animals. Trehalose is useful in preventing denaturation of a wide variety of substances including proteins, viruses and foodstuffs during desiccation and subsequent storage partly because it has a relatively high glass transition temperature (ca 120° C. in the anhydrous state) (U.S. Pat. No. 4,891,319; U.S. Pat. No. 5,149,653; U.S. Pat. No. 5,026,566). Trehalose also stabilises enzymes (Argall and Smith (1993) Biochem. Mol. Biol. Int. 30; 491). Trehalose can also form dehydrate trehalose that can further release moisture to biological compounds (Cryo-letters 16; 181-186 (1995). Trehalose and a wide variety of stabilising polyols have also been found to be useful in improving the preservation of freeze-dried samples, especially in cases where the sample is prone to loss of activity during the freeze-drying process. Other sugars useful in lyophilisation techniques include sucrose and lactose.

The present invention provides a gentle method of preserving an active agent, which is particularly useful if the active agent is labile and prone to loss of activity during a more conventional drying process. The process comprises the steps of preparing a preservation sample by dissolving/suspending an active agent in a solution of a stabilising agent; subjecting the preservation sample to such temperature and pressure conditions that the preservation sample looses solvent by evaporation, without the sample freezing or bubbling to form a foam; and removing solvent until the preservation sample dries to form a highly viscous liquid. By using a stabilising agent with two components, a glass forming polyol and a second component which decreases the rate of flow of the highly viscous liquid the resultant highly viscous liquid is less likely to move from the bottom of a vial. This results in a cosmetically superior appearance and the avoidance of reconstitution problems which may arise if the highly viscous liquid becomes displaced. In addition, movement of the highly viscous liquid from the bottom of a vial can result in crystallisation of the highly viscous liquid on contact with for instance the stopper.

DETAILED DESCRIPTION

The method of the invention is used for preserving an active agent and comprises the steps of:

a) preparing a preservation sample by dissolving/suspending an active agent in a solution of a stabilising agent;
b) subjecting the preservation sample to such temperature and pressure conditions so that the preservation sample looses solvent by evaporation, without freezing or bubbling involved in foam formation, to form a viscous liquid; and
c) further subjecting the preservation sample to such temperature and pressure conditions so that the viscous liquid dries to form a highly viscous liquid;

wherein the stabilizing agent comprises a glass forming polyol and a second component which decreases the flow rate of the highly viscous liquid formed in step c) compared to a highly viscous liquid obtained using a stabilising agent comprising the glass forming polyol in the absence of the second component.

The method of the invention produces a form of the active agent that is able to withstand extended storage during which the activity and/or antigenicity and/or immunogenicity of the active agent is maintained. Preferably the active agent retains at least 40, 50, 60, 70, preferably 80, 90, 95% of its original activity, antigenicity and/or immunogenicity over a period of at least 3, 6, 9, 12, 24 months storage at 4° C., 20° C. or 37° C. Antigenicity or immunogenicity can be measured by standard assays as described below.

The method is particularly useful for extending the shelf life of labile products which rapidly loose activity when stored in solution or when exposed to freezing or bubbling to form a foam.

A labile product is prone to loss of activity and/or to loss of antigenicity and/or loss of immunogenicity, following storage in solution and/or freezing and/or subjecting to stresses such as those involved in bubbling during foam formation.

It is particularly applicable for use where a lower concentration (e.g. 3%-15% w/v) of the glass forming polyol is advantageous and a shorter drying process (less than 4, 6, 8, 10 or 12 hours) is preferred.

A viscous liquid is defined as the product of the primary phase of solvent removal, at the end of which the majority of solvent has been lost from the sample. This point can be recognised because the rate of evaporation slows down so that the temperature of the sample returns to the shelf temperature as the endothermic effect of bulk evaporation is lost.

A highly viscous liquid is produced after the viscous liquid produced at the end of the primary phase of drying has been exposed to reduced pressure for a further period of time after the end of the primary phase of drying. A highly viscous liquid has a solvent content less than or equal to 15, 12, 10, 8, 5, 4, 3, 2 or 1% (w/w), preferably as determined by Karl Fischer coulometric moisture analyser (Eur. J. Pharm. Biopharm. (2000) 50; 277-284). The Berghof method can also be used to determine relative humidity. This method is similar to Karl Fischer but takes place under nitrogen flow rather than air flow. Preferred ranges of solvent content are 1-3%, 3-5%, 5-10% or 10-15% (w/w). The highly viscous liquid has a sufficiently low solvent content such that the active agent is preserved in a stable state for at least 3, 6, 9, 12 or 24 months at 4° C., allowing the active agent to retain at least 40, 50, 60, preferably 70, 80, 90, 95% of its activity and/or antigenicity and/or immunogenicity over this period. Preferably, the highly viscous liquid has a solid appearance but is a rubber or glass, preferably a glass and is able to flow very slowly over a period of 2, 4, or 6 days, preferably 1, 2, 3 or 4 weeks, more preferably 2, 4, 6, 8, 10 or 12 months. The extremely slow flow may be measured by inverting a receptacle containing the highly viscous liquid and leaving at room temperature until the highly viscous liquid is observed to flow. In a preferred embodiment, the highly viscous liquid will not appear to flow after 2, 4 or 6 days, preferably 1, 2, 3, or 4 weeks, more preferably 2, 4, 6, 8, 10 or 12 months in an inverted position. Preferably the highly viscous liquid has a clear, transparent appearance.

Preparation of the Preservation Sample

A preservation sample is made by dissolving/suspending an active agent in a solution of stabilising agent. The stabilising agent comprises a glass forming polyol. Preferably the stabilising polyol enables the active agent to be stored without substantial loss of activity by denaturation, aggregation or other means. Preferably, the glass forming polyol is a carbohydrate or derivatives thereof, such as glucose, maltulose, iso-maltulose, lactulose, sucrose, maltose, lactose, iso-maltose, maltitol, lactitol, palatinit, trehalose, raffinose, stachyose, melezitose or dextran.

The stabilising agent used in the methods of the invention comprises a second component. The second component decreases the flow rate of the highly viscous liquid formed by the method of the invention, in comparison with the flow rate of the highly viscous liquid produced where the stabilising agent is made up solely of the glass forming polyol.

The second component is preferably a sugar, more preferably comprising a straight chain component.

The second component is preferably a sugar with a lower moisture sorption isotherm compared to the glass forming polyol. See Fakes et al (2000) PDA J. Pharm. Sci. Technol. 54; 144-149 for examples of such sugars and for the definition of moisture sorption isotherm. Such a sugar acts by reducing the solvent content of the highly viscous liquid and hence the flow rate.

Preferably, the second component comprises a sugar selected from the group consisting of mannitol, raffinose, lactitol, sorbitol, lactose and lactobionic acid or mixtures thereof.

Preferred combinations of glass forming polyol and second component include sucrose and mannitol, sucrose and a mixture of mannitol and lactose, sucrose and raffinose, trehalose and mannitol, trehalose and a mixture of mannitol and lactose, trehalose and raffinose, maltose and mannitol, maltose and a mixture of mannitol and lactose, maltose and raffinose.

The relative amount of glass forming polyol and second component in the stabilising agent is a factor in determining the flow rate of the highly viscous liquid. Increased amounts of the second component leads to a lower flow rate in the resultant highly viscous liquid. However, the inclusion of some second components at too high a level can result in crystallisation of the dried sample which can adversely affect the activity of a labile active agent. Preferably, the ratio (w/w) of glass forming polyol and the second component in the stabilising agent is between 6:1 and 1:1, more preferably it is between 4:1 and 2:1 or 2:1 and 1:1.

Bacterial polysaccharides may advantageous make up part of the stabilising agent in a method of the invention since they can act both as a stabilising agent and an immunogen.

Amino acids can act as stabilising agents and are used in combination with a glass forming polyol. Preferred amino acids include glycine, alanine, arginine, lysine and glutamine although any amino acid, or a combination of amino acids, peptide, hydrolysed protein or protein such as serum albumin can act as part of a stabilising agent.

The concentration of the stabilising agent used in the process of the invention may be between 1% and 50% weight/volume, preferably 1-5%, 5-10%, 5-10%, 15-20%, 20-25% or 25-50%, most preferably less than or equal to 15% or 10% (w/v). The amounts of stabilising agent required is proportional to the amount of salts present. Therefore, although levels of stabilising agent between 2% and 10% are preferred, higher concentrations of 10% to 25% may be required to dry samples with a high salt (over 100 mM, 200 mM, 300 mM, 400 mM or 500 mM) content.

Preferably, the preservation sample will contain a component capable of inhibiting crystal formation in the highly viscous liquid of the invention. Salts and other molecules including amino acids and phenol red inhibit crystal formation.

Container

Different mixtures and various container shapes and sizes can be processed simultaneously. Ideally, the container size used is sufficient to contain the initial mixture and accommodate the volume of the solid formed thereof. Typically, this is determined by the mass of the glass forming material, the surface area of the container and the conditions of the glass formation. The mass of glass forming material must be sufficient to give viscous syrup which translates practically as a minimal mass per unit area of container surface. This ratio varies from mixture to mixture and container used, but is easily determined empirically by one skilled in the art by following the procedures set forth herein. Any such vials can be used, including Wheaton moulded and tube-cut vials.

The process of the invention preferably uses containers with a solvent repellent, preferably a water repellent interior surface. This is achieved through coating the interior surface with a hydrophobic composition, for instance by siliconisation. Siliconisation is achieved by processes that are well known to those skilled in the art. In one method, the container is siliconised by rising the interior of the container with an emulsion of silicone, followed by processing through an oven at high temperature, typically 350° C. (curing). Alternatively, the water repellent interior surface is achieved by the container being made of a water repellent composition.

The water repellent interior surface of the container makes the dried product of the process easier to reconstitute since less of the water collects on the sides of the container.

Although singular forms may be used herein, more than one glass matrix-forming material, more than one additive, and more than one substance may be present. Effective amounts of these components are easily determined by one skilled in the art.

Solution

The solvent into which the stabilising agent and active agent are mixed can be aqueous, organic, or a mixture of both. Sufficient aqueous solvent to dissolve the glass matrix-forming material and sufficient organic solvent to dissolve a hydrophobic substance may be used, allowing the formation of glass incorporating hydrophobic substance(s).

The choice of solvent will depend upon the nature of the material chosen for glass matrix formation, as well as the nature of any additive and/or substance to be incorporated. The solvent should be of a nature and of sufficient volume to effect adequate solubilization of the glass matrix-forming material as well as any additive and/or substance. If the substance is a hydrophilic material, the liquid will preferably be aqueous to avoid any potential loss of activity due to deleterious solvent interactions. Preferably, the aqueous solvent includes any suitable aqueous solvent known in the art, including, but not limited to, water and biological buffer solutions.

Preferably, the aqueous solvent is present in an amount of 5 to 98% by volume, more preferably 80-98% by volume, most preferably 85-98% by volume.

The volume of solvent can vary and will depend upon the glass matrix-forming material and the substance to be incorporated as well as any additives. The minimum volume required is an amount necessary to solubilise the various components. However, homogeneously dispersed suspensions of the substance(s) can also be used. Suitable amounts of the components in specific embodiments are easily determinable by those skilled in the art in light of the examples provided herein.

Various additives can be introduced into the preservation sample. A preferred additive is an inhibitor of the Maillard reaction. Preferably, if the substance and/or glass matrix-forming material contains carbonyl and amino, imino or guanidino groups, the compositions further contain at least one physiologically acceptable inhibitor of the Maillard reaction in an amount effective to substantially prevent condensation of amino groups and reactive carbonyl groups in the composition. The inhibitor of the Maillard reaction can be any known in the art. The inhibitor is present in an amount sufficient to prevent, or substantially prevent, condensation of amino groups and reactive carbonyl groups. Typically, the amino groups are present on the substance and the carbonyl groups are present on the glass matrix forming material, or the converse. However, the amino acids and carbonyl groups may be intramolecular within either the substance or the carbohydrate.

Various classes of compounds are known to exhibit an inhibiting effect on the Maillard reaction and hence to be of use in the compositions descried herein. These compounds are generally either competitive or non-competitive inhibitors of the Maillard reaction. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known non-competitive inhibitors. These include, but are not limited to, aminoguanidine and derivatives and amphotericin B. EP-A-0 433 679 also describes suitable Maillard inhibitors which include 4-hydroxy-5,8-dioxoquinoline derivatives.

It is advantageous to incorporate a coloured dye into the preservation sample in order to allow easier visualisation of the dried product of the method of the invention. This is particularly important during reconstitution to ensure that the highly viscous liquid is thoroughly reconstituted prior to use. Preferably, the coloured dye maintains its colour at a neutral pH and is compatible with injection into a patient. Most preferably the coloured dye is phenol red.

Loss of Solvent by Evaporation (Evaporative Drying—Step b)

The process of the invention involves subjecting the preservation sample to such pressure and temperature conditions so that the preservation sample looses solvent by evaporation, without the sample freezing or bubbling to form a foam.

The temperature within the preservation sample will, at times, be different from that external to the sample due to the endothermic nature of the evaporation process. References to temperature are to the conditions external to the preservation sample, for instance, where a large industrial freeze dryer is used, to the temperature of the shelf. This usually corresponds to the freeze dryer temperature setting.

Optionally a preliminary step of degassing the preservation sample is present in the method of the invention. The pressure is reduced to at or below 200 mBars, preferably between 200 and 35 mBars, for a period of at least 5 minutes before the pressure is reduced further.

A preferred embodiment of the invention achieves evaporative drying by reducing the pressure while controlling the temperature conditions. The pressure is adjusted to at or below 30, 25, 20, preferably 15, 12, most preferably 10, 8, 7, 6, 5, 4, 3, 2 or 1 mbar, while maintaining the temperature setting at a temperature above 0° C., preferably of between 5° C. to 37° C., 4° C. to 10° C., 10° C. to 15° C.; 15° C. to 25° C.; 15° C. to 20° C.; 20° C. to 25° C.; 25° C. to 30° C.; 30° C. to 37° C. or 37° C. to 45° C. These conditions are maintained for at least 1, 2, 3, 4, 5, 8, 10, 12, 16 or 24 hours, preferably for between 2-4 hours, 4-6 hours, 6-8 hours, 8-12 hours or 12-18 hours. In a particularly preferred embodiment, the pressure is maintained above 2 mbars where the temperature setting is 15° C. in order to prevent freezing of the sample. In a preferred embodiment, the temperature is maintained at 20° C. and the pressure is set to between 5-10 mBars, more preferably 6-9 mBars, most preferably around 8 mBars. Where a higher temperature setting is used, slightly lower pressure is possible without freezing the sample and where a lower temperature setting is used, the pressure should be maintained at a higher level to prevent freezing. Preferably the conditions are maintained for a sufficient period of time so that the evaporation rate has slowed so that the temperature of the sample is approximately the same as that external to the sample.

Preferably, the preservation sample does not freeze or bubble/boil to form a foam and looses solvent to form a viscous liquid or a highly viscous liquid.

Removing Solvent to Form a Highly Viscous Liquid

A subsequent stage of the method of the invention involves removing solvent until the preservation sample dries to form a highly viscous liquid. The sample neither freezes nor bubbles to form a foam during the secondary drying phase.

A highly viscous liquid is defined as a material with a solvent content less than or equal to 15, 12, 10, more preferably 8, 5, 4, 3, 2 or 1% (w/w) preferably measured using a Karl Fischer coulometric moisture analyzer. The highly viscous liquid has a sufficiently low solvent content such that the active agent is preserved in a stable state for at least 3, 6, 9, 12 or 24 months at 4° C., allowing the active agent to retain at least 40, 50, 60, preferably 70, 80, 90, 95% of its activity and/or antigenicity and/or immunogenicity over this period. Preferably, the highly viscous liquid has a solid, and/or clear appearance but is a fragile organic glass or intermediate rubbery state and is able to flow very slowly over a period of 2, 4, or 6 days, preferably 2, 3 or 4 weeks, more preferably 2, 4, 6, 8, 10 or 12 months. The extremely slow flow may be measured by inverting a receptacle containing the highly viscous liquid and leaving at room temperature or 4° C. until the highly viscous liquid is observed to flow. In a preferred embodiment, the highly viscous liquid will not appear to flow after 2, 4 or 6 days, preferably 2, 3 or 4 weeks, more preferably 2, 4, 6, 8, 10 or 12 months in an inverted position.

In one embodiment of the invention, this is achieved by maintaining the pressure and temperature conditions at those applied in the first evaporative drying stage. For instance, the pressure is maintained at or below at or below 30, 25, 20, preferably 15, 12, most preferably 10, 8, 7, 6, 5, 4, 3, 2 or 1 mbar, while maintaining the temperature setting at a temperature above 0° C., preferably of between 5° C. to 37° C., 5° C. to 10° C., 10° C. to 15° C.; 15° C. to 20° C.; 20° C. to 25° C.; 25° C. to 30° C.; or 30° C. to 37° C. For a temperature setting of 15° C., a pressure of 5-10 mBars, preferably 6-9 mBars, most preferably around 8 mBars is maintained for between 4-24 hours, preferably 1-4, 4-8, 8-12 or 12-16 hours. These temperature and pressure conditions are maintained for 1, 2, 3, 4, 5, 6, 8, 10, 12, 18 hours or more in order to obtain a highly viscous liquid with a solvent content less than or equal to 15, 12, preferably 10, 8, 5, 4, 3, 2 or 1% (w/w) preferably measured by a Karl Fischer coulometric moisture analyser.

Another embodiment of the invention increases the temperature setting during solvent removal to a higher temperature setting than that maintained earlier in the process. This allows the solvent to leave the sample at a quicker rate so that the method of the invention can be completed in a shorter time. For instance, the temperature setting is increased to above 0° C., more preferably above 20° C., preferably between 5° C. and 37° C., 5° C. and 10° C., 10° C. and 20° C.; 20° C. and 30° C.; more preferably 30° C. and 40° C.; more preferably 40° C. and 50° C.; most preferably 50° C. and 60° C. while maintaining the pressure at or below 30, 25, 20, preferably 15, 12, most preferably 10, 8, 7, 6, 5, 4, 3, 2 or 1 mbar. These temperature and pressure conditions are maintained for at least 1, 2, 3, 4, 5, 6, 8, 10, 12 or 18 hours or more in order to obtain a solid with solvent content less than or equal to 15, 12, 10, 8, 5, 4, 3, 2 or 1% (w/w) preferably measured by a Karl Fischer coulometric moisture analyser. This embodiment requires the active agent to be heat stable at the temperature used for the method to be carried out successfully.

A preferred embodiment of the invention reduces the pressure setting during solvent removal (step c) to a lower pressure setting than that used earlier in the process (step b). This allows the solvent to leave the sample at a quicker rate so that the method of the invention can be completed in a shorter time. It also enables a higher proportion of the solvent to be lost. For instance, the pressure setting is set to at or below 7, 6, preferably 5, 4, 3, more preferably 2, 1.5, 1, most preferably 0.8, 0.5, 0.2, 0.1, 0.05, 0.02, 0.01, or 0.005 mbar, while maintaining the temperature at or above 0° C., preferably between 10° C. and 20° C.; 20° C. and 30° C.; 30° C. and 35° C. or above 40° C. These temperature and pressure conditions are maintained for 1, 2, 3, 4, 5, 6, 8, 10, 12 or 18 hours or more in order to obtain a solid with a solvent content less than or equal to 15, 12, preferably 10, 8, 5, 4, 3, 2 or 1% (w/w) preferably as determined by Karl Fischer coulometric moisture analyser (Eur. J. Pharm. Biopharm. (2000) 50; 277-284).

Preferably, steps b) and c) [or b) alone] should be completed in a time equal to or less than 18 hours, preferably 16, 12, 10 hours, most preferably 8, 6, 5 or 4 hours.

Active Agent

The method of the invention is useful for preserving any active agent however it is particularly useful in the case of labile active agents that loose activity and/or antigenicity and/or immunogenicity during other preservation processes.

The active agent to be preserved using a method of the invention may comprise a biological system selected from the group consisting of cells, subcellular compositions, bacteria, outer membrane vesicle preparations and viruses, virus components or virus like particles. It may also comprise molecules, for instance proteins, peptides, amino acids, polynucleic acids, oligonucleotides, polysaccharides, oligosaccharides, polysaccharide—protein conjugates, oligosaccharide-protein conjugates.

Examples of active agents that can be preserved using a method of the invention include any bioactive substances such as pharmaceutically effective substances, including, but not limited to, antiinflammatory drugs, analgesics, tranquillisers, antianxiety drugs, antispasmodics, antidepressants, antipsychotics, tranquillisers, antianxiety drugs, narcotic antagonists, antiparkinsonism agents, cholinergic agonists, chemotherapeutic drugs, immunosuppressive agents, antiviral agents, antimicrobial agents, appetite suppressants, anticholinergics, antimetrics, antihistaminics, antimigraine agents, coronary, cerebal or peropheral vasodilators, hormonal agents, contraceptives, antithrombotic agents, diueretics, antihypertensive agents, cardiovascular drugs, opioids, and the like.

Suitable agents also include therapeutic and prophylactic agents. These include, but are not limited to, any therapeutically effective biological modifier. Such substances include, but are not limited to, subcellular compositions, cells, bacteria, outer membrane vesicle preparations, viruses and molecules including but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids, small molecules and physiologically active analogues thereof. Further, the modifiers may be derived from natural sources or made by recombinant or synthetic means and include analogues, agonists and homologs.

As used herein "protein" refers also to peptides and polypeptides. Such proteins include, but are not limited to, enzymes, biopharmaceuticals, growth hormones, growth factors, insulin, antibodies, both monoclonal and polyclonal and fragments thereof, interferons, interleukins and cytokines.

Therapeutic nucleic acid-based agents prepared by the methods described herein are also encompassed by the invention. As used herein, "nucleic acids" includes any therapeutically effective nucleic acids known in the art including, but not limited to DNA, RNA, and physiologically active analogues thereof. The nucleotides may encode genes or may be any vector known in the art of recombinant DNA including, but not limited to, plasmids, retroviruses and adeno-associated viruses.

The preservation of substances which are prophylactically active and carriers thereof are further encompassed by the invention. Preferable compositions include immunogens such as vaccines. Vaccines may be for oral administration or may be for injection after reconstitution. Suitable vaccines include, but are not limited to, live and attenuated viruses, nucleotide vectors encoding antigens, live and attenuated bacteria, protein, polysaccharide, oligosaccharide and/or lipopolysaccharide antigens, antigens plus adjuvants and antigens and/or haptens coupled to carriers. Particularly preferred are vaccines effective against diptheria, tetanus, pertussis, botulinum, cholera, Dengue, Hepatitis A, B, C and E, *Haemophilus influenzae* b, *Streptococcus pneumoniae, Neisseria meningitidis, Neisseria gonorrhoeae, Staphylococcus aureus, Staphylococcus epidermidis*, Group B streptococci, Group A streptococci, herpes virus, *Helicobacterium pylori*, influenza, Japanese encephalitis, meningococci A, B, C, Y, W, measles, mumps, papilloma virus, pneumococci, polio virus, inactivated polio virus (IPV—preferably comprising types 1, 2 and 3 as is standard in the vaccine art, most preferably the Salk polio vaccine), rubella, rotavirus, respiratory syncytial virus, Shigella, tuberculosis, varicella-zoster virus, yellow fever and combinations thereof. The antigenic component of vaccines may also be produced by molecular biology techniques to produce recombinant peptides or fusion proteins containing one or more portions of a protein derived from a pathogen. For instance, fusion proteins containing an antigen and the B subunit of cholera toxin have been shown to induce an immune response to the antigen. Sanches et al (1989) Proc. Natl. Acad. Sci. USA 86:481-485. Vaccines are particularly suitable for incorporation into the single-dosage composition. They are stable indefinitely under ambient conditions and can be redissolved in sterile diluent immediately before inoculation.

In a preferred embodiment, the active agent comprises capsular polysaccharides derived from one or more of serogroups A, C, W-135 and Y of *Neisseria meningitidis*. A further preferred embodiment comprises capsular polysaccharides derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment contains the PRP capsular polysaccharides of *Haemophilus influenzae* type b. A further preferred embodiment contains the Type 5, Type 8, 336 or PNAG (preferably deacetylated PNAG) capsular polysaccharides of *Staphylococcus aureus*. A further preferred embodiment contains the Type I, Type II, Type III or PNAG (preferably deacetylated PNAG) capsular polysaccharides of *Staphylococcus epidermidis*. A further preferred embodiment contains the Type Ia, Type Ic, Type II or Type III capsular polysaccharides of Group B streptocoocus. A further preferred embodiment contains the capsular polysaccharides of Group A streptococcus, preferably further comprising at least one M protein and more preferably multiple types of M protein.

In one embodiment of the invention, the bacterial polysaccharides are full length, being purified native polysaccharides. In an alternative embodiment of the invention, the polysaccharides are sized between 2 and 20 times, preferably 2-5 times, 5-10 times, 10-15 times or 15-20 times, so that the polysaccharides are smaller in size for greater manageability. Oligosaccharides are used in a further embodiment. Oligosaccharides typically contain between 2 and 20 repeat units.

Polysaccharide and oligosaccharides may be unconjugated or conjugated as described below.

Combinations of two or more of the above active agents may be preserved using the method of preservation of the invention. Part or all of a vaccine may be preserved using the method of preservation of the invention.

A preferred active agent to be preserved using the process of the invention comprises IPV (an inactivated mixture of polio virus strains). IPV, particularly the type 3 component, is sensitive to conventional freeze drying and foam drying techniques as shown by the loss of antigens following freeze drying or foam drying and subsequent reconstitution.

IPV is defined as inactivated polio virus (preferably comprising types 1, 2 and 3 as is standard in the vaccine art, most preferably the Salk polio vaccine). A vaccine dose of IPV contains 20-80, preferably 40 or 80 D-antigen units of type 1 (Mahoney), 4-16, preferably 8 or 16 D-antigen units of type 2 (MEF-1) and 20-64, preferably 32 or 64 D-antigen units of type 3 (Saukett).

When dried by a method of the invention, preferably the antigenicity of 1, 2, or all 3 of types 1, 2 and 3 of polio virus are retained; more preferably the antigenicity of type 1; type 2; type 3; type 1 and type 2; type 1 and type 3; type 2 and type 3; or type 1, type 2 and type 3 is retained at a level of at least 40%, 50%, 60%, 70%, 80%, 90%, 95% or 98% of the antigenicity of a reference sample which has not been subjected to the drying process. This can be measured, following reconstitution of the highly viscous liquid in an aqueous solution, by any suitable method including by ELISA using polyclonal and/or monoclonal antibodies against polio virus type 1, 2 and/or 3.

When dried by a method of the invention, preferably the immunogenicity of 1, 2, or all 3 of types 1, 2 and 3 of polio virus are retained; more preferably the immunogenicity of type 1; type 2; type 3; type 1 and type 2; type 1 and type 3; type 2 and type 3; or type 1, type 2 and type 3 is retained at a level of at least 40%, 50%, 60%, 70%, 80%, 90%, 95% or 98% of the immunogenicity of a reference sample which has not been subjected to the drying process. This can be measured, following reconstitution of the highly viscous liquid in an aqueous solution, by any suitable method. In a preferred method, the highly viscous liquid is reconstituted in an aqueous solution and is inoculated into an animal, preferably a rat. After a suitable period of time, antisera are collected from the inoculated animals and seroconversion is tested. Preferably, a relative potency of at least 0.4, 0.5, 0.6, 0.7, 0.8 or 0.9 is achieved, compared to an undried reference sample.

Preferably, IPV is combined with one or more of *Haemophilus influenzae* type b (Hib) PRP polysaccharide or oligosaccharide and/or meningococcal A, C, W and/or Y polysaccharides or oligosaccharide and/or pneumococcal polysaccharides or oligosaccharide. Most preferably the active agents comprise, IPV and Hib; IPV and MenC; IPV, Hib and MenC; Hib and MenC; IPV and MenA and C; Hib and Men A and C; IPV, Hib, Men A and C; Hib, Men C and Y; IPV, Hib, Men C and Y; IPV and MenW; or IPV, Hib and MenW.

The above particularised active agents may also comprise one or more pneumococcal capsular polysaccharides as described below.

In the above compositions where polysaccharides are used, oligosaccharides may also be employed (as defined below).

Although these compositions may be adjuvanted (as described below), they are preferably unadjuvanted or preferably do not comprise aluminium salts.

Preferably the polysaccharides or oligosaccharides are conjugated to a peptide or carrier protein comprising T-helper epitopes (as described below).

Additional Components

The preferred combinations, dried by the process of the invention may be combined with further antigens in a combination vaccine. The further antigen are either desiccated or are preferably a liquid formulation which can be used to reconstitute the dried components (highly viscous liquid). Preferred further antigens to be combined with the active agents or the invention include one or more of diphtheria toxoid, tetanus toxoid, whole cell pertussis (Pw), acellular pertussis (Pa) (as described below), Hepatitis B surface antigen, Hepatitis A virus, *Haemophilus influenzae* b polysaccharides, neisserial polysaccharides, *N. meningitidis* serotype B proteins, pneumococcal polysaccharides, pneumococcal proteins or any of the antigens listed below. Bacterial polysaccharides may be conjugated to a carrier protein such as tetanus toxoid, tetanus toxoid fragment C, diphtheria toxoid, CRM197, pneumolysin, Protein D (U.S. Pat. No. 6,342,224) as described below.

Active agents preserved using the process of the invention may be formulated with capsular polysaccharides derived from one or more of *Neisseria meningitidis, Haemophilus influenzae* b, *Streptococcus pneumoniae*, Group A Streptococci, Group B Streptococci, *Staphylococcus aureus* or *Staphylococcus epidermidis*. In a preferred embodiment, the further antigen comprise capsular polysaccharides derived from one or more of serogroups A, C, W-135 and Y of *Neisseria meningitidis*. A In a further preferred embodiment, the further antigens comprise capsular polysaccharides derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). In a further preferred embodiment, the further antigens contain the PRP capsular polysaccharides of *Haemophilus influenzae* type b or the Type 5, Type 8, 336 or PNAG (preferably deacetylated PNAG) capsular polysaccharides of *Staphylococcus aureus* or Type I, Type II, Type III or PIA capsular polysaccharides of *Staphylococcus epidermidis* or the Type Ia, Type Ic, Type II or Type III capsular polysaccharides of Group B streptocoocus. In a further embodiment, the further antigens contain the capsular polysaccharides of Group A streptococcus, preferably further comprising at least one M protein and more preferably multiple types of M protein.

In one embodiment of the invention, the bacterial polysaccharides are full length, being purified native polysaccharides. In an alternative embodiment of the invention, the polysaccharides are sized between 2 and 20 times, preferably 2-5 times, 5-10 times, 10-15 times or 15-20 times, so that the polysaccharides are smaller in size for greater manageability. Oligosaccharides are used in a preferred embodiment. Oligosaccharides typically contain between 2 and 20 repeat units.

Such capsular polysaccharides may be unconjugated or conjugated to a carrier protein such as tetanus toxoid, tetanus toxoid fragment C, diphtheria toxoid, CRM197, pneumolysin, Protein D (U.S. Pat. No. 6,342,224). Tetanus toxin, diphtheria toxin and pneumolysin are detoxified either by genetic mutation and/or preferably by chemical treatment.

The polysaccharide conjugate may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide activated polysaccharide derivatised with adipic acid hydrazide (ADH) to the protein carrier by Carbodiimide condensation (Chu C. et al Infect. Immunity, 1983 245 256).

Preferred pneumococcal proteins antigens are those pneumococcal proteins which are exposed on the outer surface of the pneumococcus (capable of being recognised by a host's immune system during at least part of the life cycle of the pneumococcus), or are proteins which are secreted or released by the pneumococcus. Most preferably, the protein is a toxin, adhesin, 2-component signal tranducer, or lipoprotein of *Streptococcus pneumoniae*, or fragments thereof. Particularly preferred proteins include, but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193—Briles et al.); PspC and transmembrane deletion variants thereof (WO 97/09994—Briles et al); PsaA and transmembrane deletion variants thereof (Berry & Paton, Infect Immun 1996 December; 64(12):5255-62 "Sequence heterogeneity of PsaA, a 37-kilodalton putative adhesin essential for virulence of *Streptococcus pneumoniae*"); pneumococcal choline binding proteins and transmembrane deletion variants thereof; CbpA and transmembrane deletion variants thereof (WO 97/41151; WO 99/51266); Glyceraldehyde-3-phosphate—dehydrogenase (Infect. Immun. 1996 64:3544); HSP70 (WO 96/40928); PcpA (Sanchez-Beato et al. *FEMS Microbiol Lett* 1998, 164: 207-14); M like protein, (EP 0837130) and adhesin 18627, (EP 0834568). Further preferred pneumococcal protein antigens are those disclosed in WO 98/18931, particularly those selected in WO 98/18930 and PCT/US99/30390.

Preferred Neisserial proteins to be formulated with the highly viscous liquid of the invention include TbpA (WO93/

06861; EP586266; WO92/03467; U.S. Pat. No. 5,912,336), TbpB (WO93/06861; EP586266), Hsf (WO99/31132), NspA (WO96/29412), Hap (PCT/EP99/02766), PorA, PorB, OMP85 (also known as D15) (WO00/23595), PilQ (PCT/EP99/03603), PldA (PCT/EP99/06718), FrpB (WO96/31618 see SEQ ID NO:38), FrpA or FrpC or a conserved portion in common to both of at least 30, 50, 100, 500, 750 amino acids (WO92/01460), LbpA and/or LbpB (PCT/EP98/05117; Schryvers et al Med. Microbiol. 1999 32: 1117), FhaB (WO98/02547), HasR (PCT/EP99/05989), lipo02 (PCT/EP99/08315), MitA (WO99/57280) and ctrA (PCT/EP00/00135). Neisserial proteins are preferably added as purified proteins of as part of an outer membrane preparation.

The highly viscous liquid is preferably formulated with antigens providing protection against one or more of Diphtheria, Tetanus and *Bordetella pertussis* infections. The pertussis component may be killed whole cell *B. pertussis* (Pw) or acellular pertussis (Pa) which contains at least one antigen (preferably two or all three) from PT, FHA and 69 kDa pertactin. Certain other acellular vaccines also contain agglutinogens such as Fim2 and Fim 3 and these vaccines are also contemplated for use in the invention. Typically, the antigens providing protection against Diphtheria and Tetanus are Diphtheria toxoid and tetanus toxoid. The toxoids are chemically inactivated toxins (for example, following treatment with formaldehyde) or toxins inactivated by the introduction of one or more point mutations.

Alternatively the highly viscous liquid of the invention may be provided as a kit with the highly viscous liquid glass in one container and liquid DTPa or DTPw in another container. Such kits can for example comprise a dual chamber syringe with the dried and liquid components contained in the same syringe but in different chambers. The dried component is then reconstituted with the liquid vaccine immediately prior to injection as a single vaccine. Thus for example, the highly viscous liquid composition of the invention is reconstituted with the liquid DTPa or DTPw vaccine (preferably extemporaneously) and administered as a single vaccine. The DTPa or DTPw vaccine typically is adjuvanted at least in part with aluminium hydroxide (for instance Infanrix® and Tritanrix® vaccines of GlaxoSmithKline Biologicals s.a.).

The highly viscous liquid is optionally formulated with one or more antigens that can protect a host against non-typeable *Haemophilus influenzae*, RSV and/or one or more antigens that can protect a host against influenza virus.

Preferred non-typeable *H. influenzae* protein antigens include Fimbrin protein (U.S. Pat. No. 5,766,608) and fusions comprising peptides therefrom (eg LB1 Fusion) (U.S. Pat. No. 5,843,464-Ohio State Research Foundation), OMP26, P6, protein D, TbpA, TbpB, Hia, Hmw1, Hmw2, Hap, and D15.

Preferred influenza virus antigens include whole, live or inactivated virus, split influenza virus, grown in eggs or MDCK cells, or Vero cells or whole flu virosomes (as described by R. Gluck, Vaccine, 1992, 10, 915-920) or purified or recombinant proteins thereof, such as HA, NP, NA, or M proteins, or combinations thereof.

Preferred RSV (Respiratory Syncytial Virus) antigens include the F glycoprotein, the G glycoprotein, the HN protein, the M protein or derivatives thereof.

It should be appreciated that antigenic compositions of the invention may comprise one or more capsular polysaccharide from a single species of bacteria. Antigenic compositions may also comprise capsular polysaccharides derived from one or more species of bacteria.

Immunogenic Compositions and Vaccines

A further aspect of the invention includes immunogenic compositions or vaccines comprising the highly viscous liquid of the invention and a pharmaceutically acceptable excipient.

Preferably, the immunogenic composition or vaccine contains an amount of an adjuvant sufficient to enhance the immune response to the immunogen. Suitable adjuvants include, but are not limited to, aluminium salts, squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polphosphazene and derivatives, and immunostimulating complexes (IS-COMs) such as those described by Takahashi et al. (1990) Nature 344:873-875. For veterinary use and for production of antibodies in animals, mitogenic components of Freund's adjuvant can be used.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered. Such factors are known in the vaccine art and it is well within the skill of immunologists to make such determinations without undue experimentation.

The active agent can be present in varying concentrations in the highly viscous liquid or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is preferably one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 ug of protein antigen, preferably 5-50 μg and most preferably 5-25 μg. Preferred doses of bacterial polysaccharides are 10-20 μg, 10-5 μg, 5-2.5 μg or 2.5-1 μg. The preferred amount of the substance varies from substance to substance but is easily determinable by one of skill in the art.

Highly Viscous Liquid Comprising an Active Agent

Another aspect of the invention is a highly viscous liquid comprising an active agent and a stabilising agent comprising a glass forming polyol and a second component which decreases the flow rate of the highly viscous liquid. Such a highly viscous liquid is preferably obtainable or obtained using a method of the invention. The active agent preferably retains its activity and/or antigenicity and/or immunogenicity following drying using the method of the invention and subsequent reconstitution. Preferably at least 40, 50, 60, 70, 80, 90, or 95% of the active agent's activity, antigenicity or immunogenicity is retained. This may be determined by any suitable method, for instance as described above.

Preferably, the glass forming polyol is a carbohydrate or derivatives thereof, including glucose, maltulose, iso-maltulose, lactulose, sucrose, maltose, lactose, iso-maltose, maltitol, lactitol, palatinit, trehalose, raffinose, stachyose, melezitose or dextran, more preferably trehalose, sucrose, sorbitol, raffinose, mannitol, lactose, lactitol or palatinit, most preferably sucrose, sorbitol, lactose or trehalose, most preferably sucrose, maltose or trehalose.

The stabilising agent present in the highly viscous liquids of the invention comprises a second component. The second component decreases the flow rate of the highly viscous liquid formed by the method of the invention, in comparison with the flow rate of the highly viscous liquid produced where the stabilising agent is made up solely of the glass forming polyol.

The second component is preferably a sugar, more preferably comprising a straight chain component.

The second component is preferably a sugar with a lower moisture sorption isotherm compared to the glass forming polyol. Such a sugar acts by reducing the solvent content of the highly viscous liquid and hence the flow rate.

Preferably, the second component is selected from the group consisting of mannitol, raffinose, lactitol, sorbitol, lactose and lactobionic acid, or mixtures thereof.

Preferred combinations of glass forming polyol and second component include sucrose and mannitol, sucrose and a mixture of mannitol and lactose, sucrose and raffinose, trehalose and mannitol, trehalose and a mixture of mannitol and lactose, trehalose and raffinose, maltose and mannitol, maltose and a mixture of mannitol and lactose, maltose and raffinose.

The relative amount of glass forming polyol and second component in the highly viscous liquid of the invention is a factor in determining its flow rate. Increased amounts of the second component leads to a lower flow rate in the resultant highly viscous liquid. However, the inclusion of some second components at too high a level can result in crystallisation which can adversely affect the activity of a labile active agent. Preferably, the ratio (w/w) of glass forming polyol and the second component in the stabilising agent is between 6:1 and 1:1, more preferably it is between 4:1 and 2:1 or 2:1-1:1.

Highly viscous liquid of the invention may contain any of the active agents described above. The active agent preserved by the highly viscous liquid may comprise a biological system, for instance cells, subcellular compositions, bacteria, outer membrane vesicle preparations and viruses. It may alternatively or further comprise a molecules, for example proteins, peptides, amino acids, polynucleic acids, oligonucleotides, polysaccharides, oligosaccharides, polysaccharide—protein conjugates, oligosaccharide-protein conjugates. It may also comprise combinations of comprising two or more of the above active agents.

Preferred embodiments include a highly viscous liquid preferably obtained or obtainable by a method of the invention wherein the active agent is or comprises a vaccine or vaccine component. Preferred components of the vaccine are described above and include IPV, more preferably IPV and bacterial polysaccharides, preferably polysaccharides or oligosaccharides from *Haemophilus influenzae* b and *Neisseria meningitidis* A, C, W and Y.

Preferred vaccine components include IPV (an inactivated mixture of polio virus strains). Preferably, IPV is combined with one or more of Hib PRP polysaccharide and/or meningococcal A, C, W and/or Y polysaccharides and/or pneumococcal polysaccharides (as described above), more preferably IPV and Hib; IPV and MenC; IPV, Hib and MenC; Hib and MenC; IPV and MenA and C; Hib and Men A and C; IPV, Hib, Men A and C; Hib, Men C and Y; or IPV, Hib, Men C and Y.

In the above compositions where polysaccharides are used, oligosaccharides may also be employed (as defined above).

Although these compositions may be adjuvanted (as described above), they are preferably unadjuvanted or preferably do not comprise aluminium salts.

Preferably the polysaccharides or oligosaccharides are conjugated to a peptide or carrier protein comprising T-helper epitopes (as described above).

The highly viscous liquid of the invention are preferably combined with other antigens in a combination vaccine which are optionally desiccated or preferably liquid formulations which can be used to reconstitute the dried components. Preferred antigens to be combined with the contents of the container of the invention include one or more of diphtheria toxoid, tetanus toxoid, whole cell pertussis (Pw), acellular pertussis (Pa) (as described above), Hepatitis B surface antigen, pneumococcal polysaccharides, pneumococcal proteins, neisserial polysaccharides, neisserial proteins. Bacterial polysaccharides may be conjugated to a carrier protein such as tetanus toxoid, tetanus toxoid fragment C, diphtheria toxoid, CRM197, pneumolysin, Protein D (U.S. Pat. No. 6,342, 224) as described above.

A further aspect of the invention is a method of making a vaccine comprising the step of reconstituting the highly viscous liquid in an aqueous solution. In a preferred embodiment, the aqueous solution comprises Diphtheria toxoid, Tetanus toxoid and Pertussis (acellular or whole cell) antigens and optionally further comprises hepatitis B surface antigen. The DTP vaccine is optionally at least in part adjuvanted with an aluminium salt, preferably aluminium hydroxide or aluminium phosphate.

Another embodiment of the invention is a kit comprising the highly viscous liquid of the invention held in a first container and a vaccine comprising liquid DTP (acellular or whole cell) in a second container. A dual chamber syringe may be used as described above.

All references or patent applications cited within this patent specification are incorporated by reference herein.

EXAMPLES

The examples below are carried our using standard techniques, which are well known and routine to those of skill in the art, except where otherwise described in detail. The examples are illustrative, but do not limit the invention.

Example 1

Establishment of Freezing Conditions

Samples were made by dissolving sucrose in water to give 1%, 5%, 10% and 20% solutions. Samples were put into a Heto Drywinner 8-85 freeze dryer in which shelf temperature may be regulated to within 1° C., the final temperature of the condenser is −85° C., pressure is regulated with a bleed valve and 6 thermocouples are available to measure the product temperature. The shelf temperature setting was maintained at 15° C. throughout the process. The pressure was initially reduced to 200 mBar and maintained at this level for 10 minutes before reducing the pressure further to 50 mBars, 5 mBars, 2.5 mBars, 0.75 mBars, 0.4 mBars and 0.2 mBars. Each pressure level was maintained for 20 minutes to allow the temperature to equilibrate and the temperature of the sample was read using a thermocouple. Thermocouples were attached to samples with different sucrose concentrations and the temperatures recorded in table 1 are mean values of the temperatures.

Results

All samples froze between 1.66 and 1.11 mbars, irrespective of the concentration of sucrose present. The temperatures measured at different pressures were very close to those predicted from the triple point curve. Therefore the presence of sucrose does not have a large effect on the temperature of the samples at different pressures.

In order to avoid freezing of the sample, the pressure should be maintained above 2 mBars for a shelf temperature of 15° C. At lower temperatures the pressure should be maintained at a higher level whereas use of a higher temperature would allow the pressure to be reduced further without the samples freezing.

TABLE 1

| Pressure | Measured temperature | Theoretical temperature | Liquid/frozen |
|---|---|---|---|
| 1000 mBar | 15° C. | | liquid |
| 50 mBar | 15° C. | | liquid |
| 5 mBar | 1° C. | 1° C. | liquid |
| 2.5 mBar | −5° C. | −7° C. | liquid |
| 0.75 mBar | −21° C. | −21° C. | frozen |
| 0.4 mBar | −22° C. | −27° C. | frozen |
| 0.2 mBar | −27° C. | −32° C. | frozen |

Example 2

Method for Drying without Freezing or Foam Formation

Preservation samples containing 5%, 10%, 15% and 25% sucrose were made and added to vials. Samples were put into a freeze dryer at a temperature setting of 15° C. throughout the process. The pressure was initially reduced to 200 mBars and maintained at this level for 10 minutes to allow degassing before reducing the pressure further. The pressure was further reduced to 8 mbars for two to three hours during which time thermocouples inside the samples showed that the sample temperature reduced to 4° C. due to evaporative cooling. After 2-3 hours, the temperature of the samples returned to 15° C., indicating that evaporation under these temperature and pressure conditions was near completion. During this stage of the process, the sample did not boil to form a foam or freeze so that an active agent within the sample is exposed to as little stress as possible. The sample have the appearance of viscous liquid.

Figure 1:
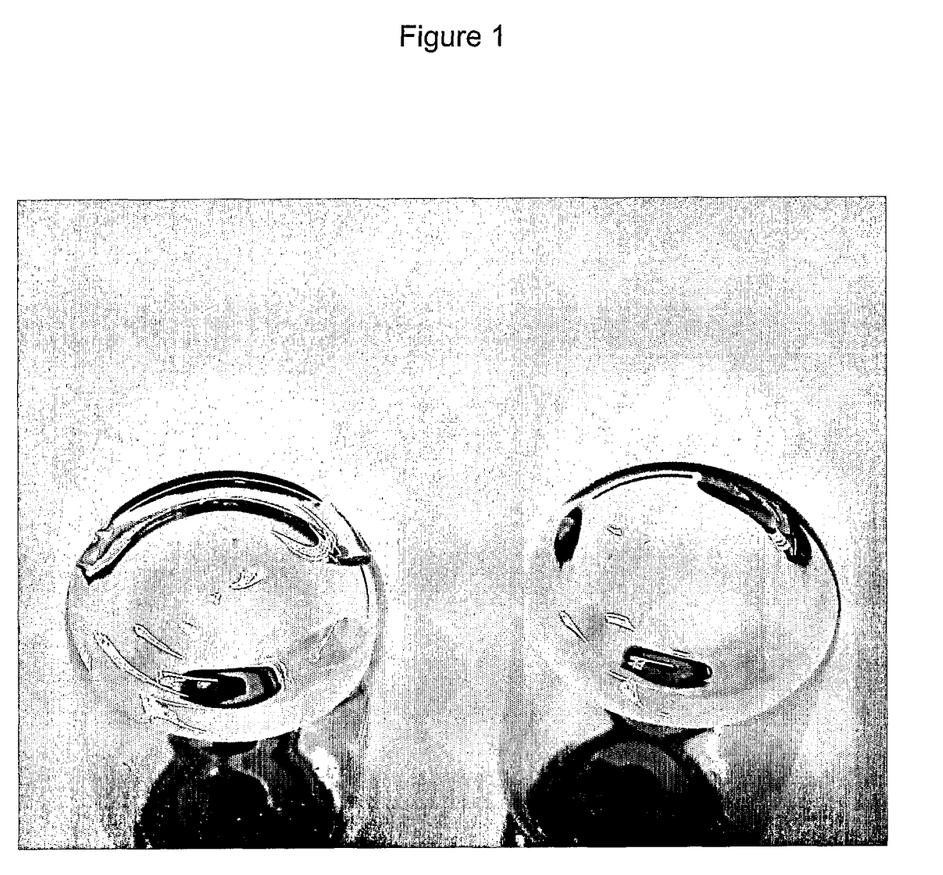
FIG. 1—Photograph of the high viscosity liquid in inverted vials.

Further drying of the samples was achieved by reducing the pressure further to 0.1 mbars while keeping the shelf temperature setting at 15° C. These conditions were maintained for a further 10-16 hours. During this phase, the sample temperature remained at 15° C. since the rate of evaporation was slow. Further drying took place and the resultant sample had a solid appearance. If the sample was place on its side, the sample contents slowed very slowly, over a period of days showing that the sample is a liquid glass of high viscosity. FIG. 1 shows the appearance of the high viscosity liquid.

Example 3

Retention of IPV Immunogenicity after Drying without Freezing or Foam Formation

Such samples have not been subjected to stresses associated with the bubbling that accompanies foam formation or freezing. Experiments were performed to determine whether this method produced a high level of antigen retention when used to dry IPV.

Three separate experiments were performed in which IPV was resuspended in an aqueous solution with 10% sucrose or 10% trehalose as the stabilising agent. The samples were put into siliconised vials which were placed into a Heto Drywinner 8-85 freeze-dryer and the temperature was set to 15° C. The pressure was initially reduced to 35 mBars to degas the sample. After 10 minutes, the pressure was further reduced to 8 mBars and was kept at this level for two hours. During this period the temperature setting was kept at 15° C. and the temperature into the sample was monitored. As water evaporated from the sample, the temperature dropped to 4° C. but towards the end of the two hours, the temperature returned to 15° C. as the rate of evaporation slowed. No bubbling or foam formation occurred under these conditions. The pressure was then reduced further to 0.1 mbars and these conditions were maintained for 16 hours more in the first two experiments and for 10 hours more in the third experiment.

The samples were reconstituted in water and an ELISA was used to assess the retention of antigenicity of the three polio virus strains. The monoclonal antibody against type 3 IPV, was used in an ELISA to assess the degree of antigen retention in the reconstituted, freeze dried sample compared to a reference sample that had not been frozen. Results are presented as a percentage of the reading given for a sample which had not undergone a drying procedure.

Results

The dried samples had a solid appearance however they appeared to be in the form of a highly viscous liquid/glass since, over a period of days, the dried sample was able to flow if the container was inverted.

TABLE 2

Retention of type 3 IPV antigen as determined by ELISA using a monoclonal antibody (drying without foaming or freezing)

| Formulation | 1$^{st}$ experiment (18 hour cycle) | 2$^{nd}$ experiment (18 hour cycle) | 3$^{rd}$ experiment (12 hour cycle) |
|---|---|---|---|
| No sugar | 0% | | |
| 2.5% sucrose | 0% | | |
| 10% sucrose | 75% | 78% | 91% |
| 10% trehalose | 82% | 79% | 93% |

These levels of type 3 IPV antigen retention compares very favourably with the freeze drying results shown below where very low values were usually found in the same ELISA format when a monoclonal antibody against type 3 was used.

TABLE 3

Retention of type 1, 2 and 3 IPV antigens as determined by ELISA using a monoclonal and polyclonal antibodies (freeze drying)

| | | ELISA—type 1/2/3% | |
|---|---|---|---|
| Method of drying | Polyol content | Polyclonal | Monoclonal |
| Freeze drying | 3.15% sucrose | 46/49/58* | 19/25/0 |
| Freeze drying | 10% trehalose | 47/43/58 | 25/0/0 |

*The experiment freeze drying in the presence of 3.15% sucrose was repeated five times and the results shown are from one representative experiment.

Example 4

Long Term Storage Stability of Dried IPV Stored as a Highly Viscous Liquid/Glass IPV dried using the method described in Example 3 was stored at 4° C. for 9 months. The samples were reconstituted in water with 150 mM NaCl and an ELISA was used to assess the retention of antigenicity of the three polio virus strains. Three monoclonal antibodies, one against each strain, were used in separate ELISAs to assess the degree of antigen retention in the reconstituted stored sample. A similar ELISA had been carried out on reconstituted samples from the same batch prior to storage. All results were compared to a reference sample that had not been dried. Results are presented as a percentage of the reading given for a sample which had not undergone a drying procedure.

Results

TABLE 4

Retention of IPV antigens after storage as a highly viscous liquid for 9 months

| Treatment | Type 1 ELISA | Type 2 ELISA | Type 3 ELISA |
| --- | --- | --- | --- |
| Dried/reconstituted Not stored | 72% | 75% | 88% |
| Dried/reconstituted 9 months 4° C. | 70% | 94% | 90% |

Therefore IPV which has been dried by the method described in Example 3 can be stored at 4° C. for at least 9 months without loss of antigenicity.

Example 5

Comparison of the Immunogenicity In Vivo of IPV After Drying to Form a Highly Viscous Liquid and Reconstitution Compared to Undried IPV Groups of 10 Wistar rats were inoculated with various dilutions of IPV which had been dried in the presence of 10% sucrose to form a highly viscous liquid using the method disclosed in Example 2 and reconstituted. Further groups of 10 Wistar rats were inoculated with reference samples of IPV which had been prepared in the same way but which had not been dried.

After 21 days, sera were taken from all the rats and the sera were tested in separate immunoprecipitation assays using Type 1, Type 2 and Type 3 polio virus.

Results are shown in table 5 that contains:—a) the number of responant rats for each IPV dilution, b) the ED50 which is the dose that is required to ensure that 50% of the rats seroconvert as assessed by the immunoprecipitation assay and c) the relative potency of the dried and reconstituted IPV compared to the undried reference IPV.

TABLE 5

Immunogenicity of IPV after drying to form a high viscosity liquid (JLE017/05) and reconstitution compared to an undried reference IPV (JLE097)

| | Number of respondant | | | | | |
| --- | --- | --- | --- | --- | --- | --- |
| Sample | undiluted | 1/ 1.25 | 1/ 3.125 | 1/ 7.81 | ED50 | RP relative potency |
| JLEO17/05 | | | | | | |
| Type 1 | 10 | 9 | 6 | 5 | 6.37 | 0.956 |
| Type 2 | 6 | 4 | 3 | 3 | 7.14 | 0.825 |
| Type 3 | 6 | 8 | 2 | 1 | 18.18 | 1.051 |
| JLE097 | | | | | | |
| Type 1 | 10 | 10 | 10 | 7 | 3.33 | 1.120 |
| Type 2 | 8 | 6 | 5 | 2 | 3.12 | 0.951 |
| Type 3 | 7 | 6 | 4 | 1 | 16.91 | 1.172 |
| Reference | | | | | | |
| Type 1 | | 10 | 8 | 4 | 6.37 | |
| Type 2 | | 7 | 5 | 2 | 2.93 | |
| Type 3 | | 5 | 3 | 0 | 22.57 | |

JLEO17/05 is a IPV batch that was dried to form a highly viscous liquid and subsequently reconstituted. The JLE097 is the undried reference.

Table 5 shows that the number of respondants inoculated with each dilution of IPV is similar between the two batches of dried and reconstituted IPV and the undried reference sample. In general, Type 1 IPV elicited the best immune response, with Type 2 eliciting an immune response in slightly fewer rats. Type 3 elicited the weakest immune response.

The process of drying to form a highly viscous liquid does not impair the ability of IPV to elicit immunoprecipitating antibodies in vivo. A relative potency (RP) reading of 1.0 indicates that the sample elicits an equivalent response to the reference sample. Both dried samples produce RP readings of close to 1.0 for all three types of polio virus indicating the drying process does not effect the ability of the sample to elicit an immune response.

Example 6

Effect of Drying to Form a Highly Viscose Liquid Using Sucrose or Trehalose as Stabilising Agent on the Ability of IPV to Elicit an Immunoprecipitating Immune Response In Vivo Groups of 10 Wistar rats were inoculated with IPV which had been dried in the presence of either 10% sucrose or 10% trehalose as described in Example 2, and then reconstituted. Further groups of 10 Wistar rats were inoculated with an equivalent amount of IPV that had not been dried, as reference samples.

After 21 days, sera were collected from all rats and an immunoneutralisation assay, as described in Example 5 was used to assess the amount of immunoneutralising antibody that had been raised against each of Type 1, Type 2 and Type 3 polio virus.

Relative potencies were calculated for each sample by comparing the immune response to that elicited by the undried reference sample.

Results are shown in Table 6.

TABLE 6

Comparison of drying in sucrose and trehalose

| Lot Number | Sugar present | Relative potency in vivo Type 1/Type 2/Type 3 | Humidity % Karl Fischer | Duration (hours) |
|---|---|---|---|---|
| Jle017 | 10% trehalose | 0.95/0.82/1.05 | nd | 7 |
| 31CO3/01 | 10% sucrose | 0.69/1.20/0.97 | 4.6% | 18 |
| 31CO3/02 | 10% trehalose | 0.60/0.94/0.9 | 11.5% | 18 |
| 03D02/01 | 10% sucrose | 0.74/1.05/0.96 | 5.9% | 12 |
| 03D02/02 | 10% trehalose | 0.58/0.98/1.06 | 10.6% | 12 |

The amount of water remaining in samples was lower when sucrose was used as stabilising agent with approximately 5% humidity remaining compared to approximately 10% when trehalose was used as the stabilising agent measured by a Karl Fischer coulometric moisture analyser.

Both sucrose and trehalose were effective at stabilising IPV during the drying process so that the reconstituted IPV gave relative potency readings approaching 1.0 for most of the different types of polio virus. The relative potencies were particularly good for Type 3 polio virus which looses its immunogenicity relatively easily.

Example 7

Measurement of Humidity by Karl Fischer

Analysis was carried out in a Karl Fischer titrometer (Aqua 30.00—Elektrochemie Halle). The sample was weighed out and placed into the oven at a setting of 80° C. The sample was flushed with nitrogen gas and then added to hydranal reagent (Riedel de Hahn) in order to perform the analysis by coulometry.

sucrose and 4% mannitol or 5% sucrose and 5% mannitol. The samples were placed into a freeze dryer and were dried using the method of example 2 to form highly viscous liquids. Briefly, the samples were degassed at below 200 mBars for 10 minutes, subjected to primary drying at 8 mBars for 4 hours and then to secondary drying at 0.1 mBars for 1, 2 or 3 hours.

The samples were inspected visually for crystalline/amorphous composition and flow rate was assessed at 25° C. by inverting the tube containing the highly viscous liquid and monitoring the time required for flowing to be observed.

Results

After the drying cycle has finished, the samples were visually inspected. The 5% sucrose/5% mannitol sample had crystallised but all other samples were amorphous glasses.

Flowing was monitored for a hour after the inversion of the tubes. The sample made from a preserving solution having 10% sucrose started to flow down the side of the vial wall after 8 minutes and had moved to the stoppered end of the vial after 30 minutes. The sample made from a preserving solution having 9% sucrose and 1% mannitol started to flow down the side of the vial wall after 20 minutes and had moved to the stoppered end of the vial after 45 minutes. The sample made from a preserving solution having 8% sucrose and 2% mannitol started to flow down the side of the vial wall after 45 minutes. The sample made from a preserving solution having 7% sucrose and 3% mannitol started to flow down the side of the vial wall after 51 minutes. The samples made from a preserving solution having 6% sucrose and 4% mannitol or 5% sucrose and 5% mannitol were not observed to flow after over an hour.

Figure 2:
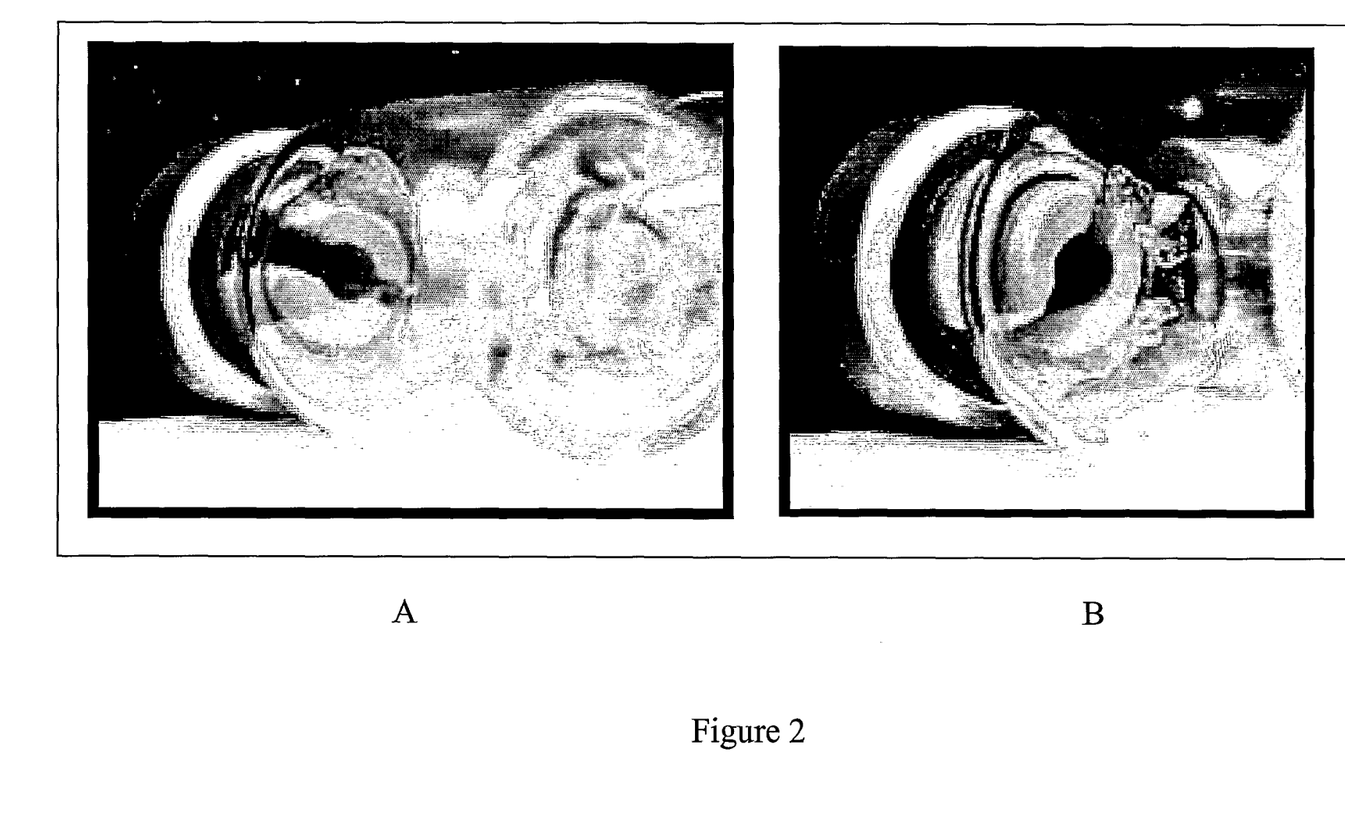
FIG. 2—Photographs of a high viscosity liquid after flowing to the stopper end of the vial. Panel A shows the high viscosity liquid surrounding the stopper. Panel B shows the eventual crystallisation of the high viscosity liquid.

After the sample made from a preserving solution containing 10% sucrose had come in contact with the halobutyl stopper, crystallisation of the sample was observed (FIG. 2).

The moisture content of the samples has assessed using the Berghof WDS400 apparatus at a temperature setting of 120° C. for 60 minutes. The results are shown in table 7.

TABLE 7

Moisture content of samples with different amounts of sucrose and mannitol

| % sucrose in samples | % relative humidity 1 hour secondary drying | % relative humidity 2 hours secondary drying | % relative humidity 3 hours secondary drying |
|---|---|---|---|
| 5 | 8.0 | 8.8 | 8.6 |
| 6 | 9.3 | 10.0 | 8.9 |
| 7 | 9.6 | 9.6 | 8.7 |
| 8 | 10.1 | 10.7 | 10.2 |
| 9 | 10.5 | 11.3 | 9.5 |
| 10 | 12.4 | 10.3 | 11.0 |

Example 8

Measurement of Humidity Using the Berghof Method

Samples are analysed using a Satorius WDS400 at an oven setting of 120° C. with the run taking 60 minutes.

Example 9

The Use of a Mixture of Sucrose and Mannitol to Preserve Hib-IPV as a Highly Viscous Liquid Samples containing Hib/IPV were suspended in solutions containing 10% sucrose, 9% sucrose and 1% mannitol, 8% sucrose and 2% mannitol, 7% sucrose and 3% mannitol, 6%

The invention claimed is:

1. A highly viscous liquid comprising a preserved active agent and a stabilising agent obtainable by a method comprising the steps of:
    a) preparing a preservation sample by dissolving and/or suspending an active agent in a solution of a stabilising agent;
    b) subjecting the preservation sample to a temperature condition above 0° C. and a pressure condition below 30 mbar so that the preservation sample loses solvent by evaporation without freezing or bubbling involved in foam formation, thereby forming a viscous liquid; and
    c) further subjecting the viscous liquid to a temperature condition above 0° C. and a pressure condition below 30 mbar thereby forming a highly viscous liquid;

wherein the stabilizing agent comprises a glass forming polyol and a second component which decreases the flow rate of the highly viscous liquid formed in step c), wherein the second component comprises a sugar with a lower moisture sorption isotherm compared to the glass forming polyol
wherein the active agent retains at least 40% of its antigenicity compared to the antigenicity of a reference sample which has not been subjected to the drying process of steps b)-c), where antigenicity is measured by ELISA.

2. The highly viscous liquid of claim 1 wherein the stabilising agent comprises sucrose or trehalose as the glass forming polyol.

3. The highly viscous liquid of claim 1 wherein the second component is a sugar comprising a straight chain component.

4. The highly viscous liquid of claim 3 wherein the second component is selected from the group consisting of mannitol, raffinose, lactitol, sorbitol and lactobionic acid.

5. The highly viscous liquid of claim 1 wherein the ratio (w/w) of glass forming polyol and the second component is between 6:1 and 1:1.

6. The highly viscous liquid of claim 5 wherein the ratio (w/w) of glass forming polyol and the second component is between 4:1 and 2:1.

7. The highly viscous liquid of claim 1 wherein the active agent comprises a molecule selected from the group consisting of protein, peptide, amino acid, polynucleotide, oligonucleotide, polysaccharide, oligosaccharide, polysaccharide-protein conjugate and oligosaccharide-protein conjugate.

8. The highly viscous liquid of claim 1 wherein the active agent comprises a biological system selected from the group consisting of cells, subcellular compositions, bacteria, viruses, virus components and virus like particles.

9. The highly viscous liquid of claim 1 wherein the active agent comprises a vaccine.

10. The highly viscous liquid of claim 1 wherein the active agent comprises Inactivated Polio Virus (IPV).

11. The highly viscous liquid of claim 1 wherein the active agent comprises a bacterial polysaccharide or oligosaccharide.

12. The highly viscous liquid of claim 11 wherein the active agent comprises Hib (*Haemophilus influenzae* b) polysaccharide or oligosaccharide.

13. The highly viscous liquid of claim 1 wherein the active agent comprises *Neisseria meningitidis* serogroup C polysaccharide or oligosaccharide.

14. The highly viscous liquid of claim 1 held within a container with a solvent repellent interior surface.

15. An immunogenic composition or vaccine comprising the highly viscous liquid of claim 1 and a pharmaceutically acceptable excipient.

16. A kit comprising the highly viscous liquid of claim 1 held in a first container and a liquid vaccine component in a second container.

17. The highly viscous liquid of claim 1 wherein the concentration of stabilising agent is less than 15%.

* * * * *